United States Patent
Yokoyama et al.

(10) Patent No.: US 8,658,012 B2
(45) Date of Patent: Feb. 25, 2014

(54) BIOSENSOR FOR ELECTROCHEMICAL MEASUREMENT OF 1,5-ANHYDROGLUCITOL, AND MEASURING METHOD AND MEASURING KIT USING THE SAME

(75) Inventors: Takao Yokoyama, Takasaki (JP); Hisako Takagi, Takasaki (JP); Yayoi Irie, Takasaki (JP); Reiko Machida, Takasaki (JP); Yoshihiko Umegae, Takasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 140 days.

(21) Appl. No.: 13/133,115

(22) PCT Filed: Dec. 7, 2009

(86) PCT No.: PCT/JP2009/070456
§ 371 (c)(1),
(2), (4) Date: Jun. 6, 2011

(87) PCT Pub. No.: WO2010/067769
PCT Pub. Date: Jun. 17, 2010

(65) Prior Publication Data
US 2011/0259762 A1 Oct. 27, 2011

(30) Foreign Application Priority Data
Dec. 8, 2008 (JP) ................. 2008-311849

(51) Int. Cl.
*G01N 27/327* (2006.01)
(52) U.S. Cl.
USPC ................. 204/403.14; 204/403.04
(58) Field of Classification Search
USPC ............ 204/403.01–403.15; 205/777.5, 778, 205/792
See application file for complete search history.

(56) References Cited

U.S. PATENT DOCUMENTS

| | | | |
|---|---|---|---|
| 5,407,806 A | 4/1995 | Yabuuchi et al. | |
| 7,288,174 B2 * | 10/2007 | Cui et al. | 204/403.14 |
| 2010/0062469 A1 * | 3/2010 | Umegae et al. | 435/25 |

FOREIGN PATENT DOCUMENTS

| | | |
|---|---|---|
| EP | 2305803 A1 | 4/2011 |
| JP | 02-268679 A | 11/1990 |
| JP | 07-067697 A | 3/1995 |
| JP | 08-070893 A | 3/1996 |
| JP | 10-062402 A | 3/1998 |
| JP | 10-084953 A | 4/1998 |
| JP | 3819094 B2 | 6/1998 |
| JP | 11-018762 A | 1/1999 |
| JP | 2872983 B2 | 3/1999 |

(Continued)

OTHER PUBLICATIONS

International Search Report mailed Feb. 23, 2010 for the corresponding PCT application No. PCT/JP2009/070456.

(Continued)

*Primary Examiner* — Alex Noguerola
(74) *Attorney, Agent, or Firm* — Leason Ellis LLP

(57) ABSTRACT

The biosensor has an electrode system for electrochemically measuring 1,5-anhydroglucitol (1,5-AG) and a reagent layer formed on said electrode system. The reagent layer contains an enzyme for measuring 1,5-anhydroglucitol, phenothiazine compounds, a stabilizer selected from a group of compounds comprising metal salts, organic acids, and amino acids, and an acidic polymer compound as an optional ingredient. The biosensor has excellent storage stability and can electrochemically measure 1,5-anhydroglucitol unaffected by the hematocrit contained in a whole blood sample.

9 Claims, 5 Drawing Sheets

(56) References Cited

FOREIGN PATENT DOCUMENTS

| | | |
|---|---|---|
| JP | 2000-135079 A | 5/2000 |
| WO | WO-91/09304 A1 | 6/1991 |
| WO | WO-96/25514 A1 | 8/1996 |
| WO | WO 2006/134870 A1 | 12/2006 |
| WO | WO-2008/072702 A1 | 6/2008 |
| WO | WO 2008/072702 A1 | 6/2008 |
| WO | WO 2009/154247 A1 | 12/2009 |

OTHER PUBLICATIONS

European Search Report mailed May 10, 2013 for the corresponding European Application No. 09831873.6.

* cited by examiner

BIOSENSOR FOR ELECTROCHEMICAL MEASUREMENT OF 1,5-ANHYDROGLUCITOL, AND MEASURING METHOD AND MEASURING KIT USING THE SAME

CROSS-REFERENCE TO RELATED PATENT APPLICATIONS

This application is a U.S. National Phase Application under 35 U.S.C. §371 of International Patent Application No. PCT/JP2009/070456, filed Dec. 7, 2009, and claims the benefit of Japanese Patent Application No. 2008-311849, filed Dec. 8, 2008, all of which are incorporated by reference herein. The International Application was published in Japanese on Jun. 17, 2010 as International Publication No. WO/2010/067769 under PCT Article 21(2).

SEQUENCE LISTING

The instant application contains a Sequence Listing which has been submitted in ASCII format via EFS-Web and is hereby incorporated by reference in its entirety. Said ASCII copy, created on Jun. 2, 2011, is named Sequence_Listing_2536.txt and is 4,550 bytes in size.

FIELD OF THE INVENTION

The present invention relates to a biosensor for electrochemically measuring 1,5-anhydroglucitol contained in a specimen including body fluid such as whole blood, a method for electrochemically measuring 1,5-anhydroglucitol using the same, and a kit for electrochemically measuring 1,5-anhydroglucitol comprising the same.

BACKGROUND OF THE INVENTION

In recent years, as dietary life has gradually become rich, the number of diabetes patients has increased. In order to prevent the development of complications in such diabetes patients, it is necessary to control their blood glucose level to a level close to those of healthy persons. As a marker for grasping the controlled state of the blood glucose level of diabetes patients, 1,5-anhydroglucitol (hereinafter abbreviated as "1,5-AG" at times) has become a focus of attention. Such 1,5-AG is advantageous in that it is insusceptible to diet and in that it reflects the blood glucose control level in a relatively short period of time, such as for the past 1 week.

Most recently, it has been revealed that 1,5-AG is a marker that reflects the postprandial hyperglycemia state, more precisely than blood glucose markers such as hemoglobin A1c.

A biosensor, which is available when a patient collects a whole blood specimen at home and then measures 1,5-AG by him/herself so as to use the measurement value as an indicator for blood glucose control level, is disclosed in each of Patent Literature 1 and Patent Literature 2, Patent Literature 1 discloses a biosensor having a blood cell separation unit and a detection unit, whereas Patent Literature 2 discloses the electrochemical measurement of 1,5-AG, in which an osmium (III) complex is used as a redox mediator and 2-sulfobenzoic acid or 3-sulfobenzoic acid is used as a stabilizer.

On the other hand, there has been known a blood glucose self-monitoring meter whereby patients are able to measure their blood glucose level by themselves at home. Such blood glucose self-monitoring meters are commercially available with trade names such as Glucocard (Arkray Inc.) or Freestyle (Nipro Corporation).

Biosensors for measuring other blood glucose markers such as glycoalbumin and hemoglobin A1e have also being developed.

CITATION LIST

Patent Literature

Patent Literature 1: WO2006/134870, pamphlet
Patent Literature 2: WO2008/072702, pamphlet

SUMMARY OF INVENTION

Technical Problem

However, the biosensor for measuring 1,5-AG, which is described in Patent Literature 1, Patent Literature 2 or the like, should have been improved in the following respects, in order to being provided as a biosensor used by patients themselves at home.

That is, during distribution or storage at home, since the biosensor is affected by environmental factors such as a wide range of temperature or humidity, it is deteriorated and thus it cannot maintain constant performance. Specifically, a biosensor, which was produced by applying a mediator and an oxidoreductase onto an electrode and then drying them, was deteriorated, as the storage period became long. As a result, the measurement value of 1,5-AG measured using such a biosensor tended to be decreased.

Moreover, when a patient measures 1,5-AG at home, he/she does not separately collect plasma for convenience, and whole blood is used in measurement. Thus, the measurement is affected by hematocrit and the like contained in the whole blood. The term "hematocrit" is used to indicate a blood cell component contained in whole blood.

Since the value of 1,5-AG is decreased if a person is affected by diabetes, the 1,5-AG value of diabetes patients becomes extremely low. In other words, a biosensor for measuring 1,5-AG is required to precisely measure a low 1,5-AG value. However, an exact 1,5-AG value cannot be measured, if the measurement is affected by the aforementioned blood components. As a result, it is likely that patients are not able to appropriately control a blood glucose level.

Furthermore, in a case in which such a blood glucose level is used to control the blood glucose of patients suffering from diabetes or postprandial hyperglycemia, their blood glucose level must be measured frequently, and thus it results in patients' inconvenience. Since glycoalbumin or hemoglobin A1c does not reflect a blood glucose control state in a short period of time such as approximately 1 week, it is inadequate to use such glycoalbumin or hemoglobin A1c as a blood glucose control marker at the ordinary home.

DETAILED DESCRIPTION OF THE INVENTION

Solution to Problem

The present inventors have conducted intensive studies directed towards solving the aforementioned problems. As a result, the inventors have found that a biosensor can be stabilized during storage by adding a certain type of stabilizer to the reagent layer of the biosensor, and that the influence of hematocrit and the like on whole blood measurement can be prevented by adding a certain type of acidic polymer compound as an optional ingredient to the biosensor, thereby completing the present invention.

Specifically, the present invention relates to the following [1] to [10]:

[1] A biosensor having an electrode system for electrochemically measuring 1,5-anhydroglucitol and a reagent layer formed on the electrode system, wherein the reagent layer comprises
   (1) a 1,5-anhydroglucitol-measuring enzyme,
   (2) a phenothiazine compound,
   (3) a stabilizer selected from the compound group consisting of metal salts, organic acids and amino acids, and
   (4) an acidic polymer compound as an optional ingredient;
[2] The biosensor according to [1] above, wherein the 1,5-anhydroglucitol-measuring enzyme is 1,5-anhydroglucitol dehydrogenase or 1,5-anhydroglucitol-6-phosphate dehydrogenase;
[3] The biosensor according to [1] or [2] above, wherein the phenothiazine compound is thionine;
[4] The biosensor according to any one of [1] to [3] above, wherein the stabilizer is one or two or more selected from the compound group consisting of sodium chloride, sodium citrate, magnesium sulfate, piperazin-1,4-bis(2-ethanesulfonic acid), o-sulfobenzoic acid cyclic, arginine or a salt thereof, glutamic acid or a salt thereof, and lysine or a salt thereof;
[5] The biosensor according to any one of [1] to [4] above, wherein the stabilizer is o-sulfobenzoic acid cyclic;
[6] The biosensor according to any one of [1] to [5] above, wherein the acidic polymer compound is a hydrocarbon compound, which has an acidic functional group and may be substituted with a fluorine atom;
[7] The biosensor according to any one of [1] to [6] above, wherein the acidic polymer compound is a perfluorosulfonic acid resin;
[8] The biosensor according to any one of [1] to [7] above, wherein the 1,5-anhydroglucitol-measuring enzyme used is 1,5-anhydroglucitol dehydrogenase derived from *Pseudomonas* sp.;
[9] A method for electrochemically measuring 1,5-anhydroglucitol contained in a specimen using the biosensor according to any one of [1] to [8] above; and
[10] A kit for electrochemically measuring 1,5-anhydroglucitol contained in a specimen, the kit comprising the biosensor according to any one of [1] to [8] above.

Advantageous Effects of Invention

According to the present invention, it becomes possible to prevent the deterioration of a biosensor due to a change in environmental factors such as a temperature applied during storage, and to produce a biosensor with improved storage stability, which suppresses a change in 1,5-AG measurement values and is able to precisely measure a low 1,5-AG value. Thus, even after long-term storage, there can be obtained the same precise 1,5-AG measurement value as that at initiation of the production. Moreover, it is also possible to provide a biosensor capable of precisely measuring a 1,5-AG value in a wide range of specimens without being affected by hematocrit and the like during whole blood measurement.

DESCRIPTION OF EMBODIMENTS

The present invention relates to a biosensor having an electrode system for electrochemically measuring 1,5-AG and a reagent layer formed on the electrode system, wherein the reagent layer comprises (1) a 1,5-AG-measuring enzyme, (2) a phenothiazine compound as a redox mediator, (3) a stabilizer selected from the compound group consisting of metal salts, organic acids and amino acids, and (4) an acidic polymer compound comprised, as necessary, as an optional ingredient.

Figure 1:
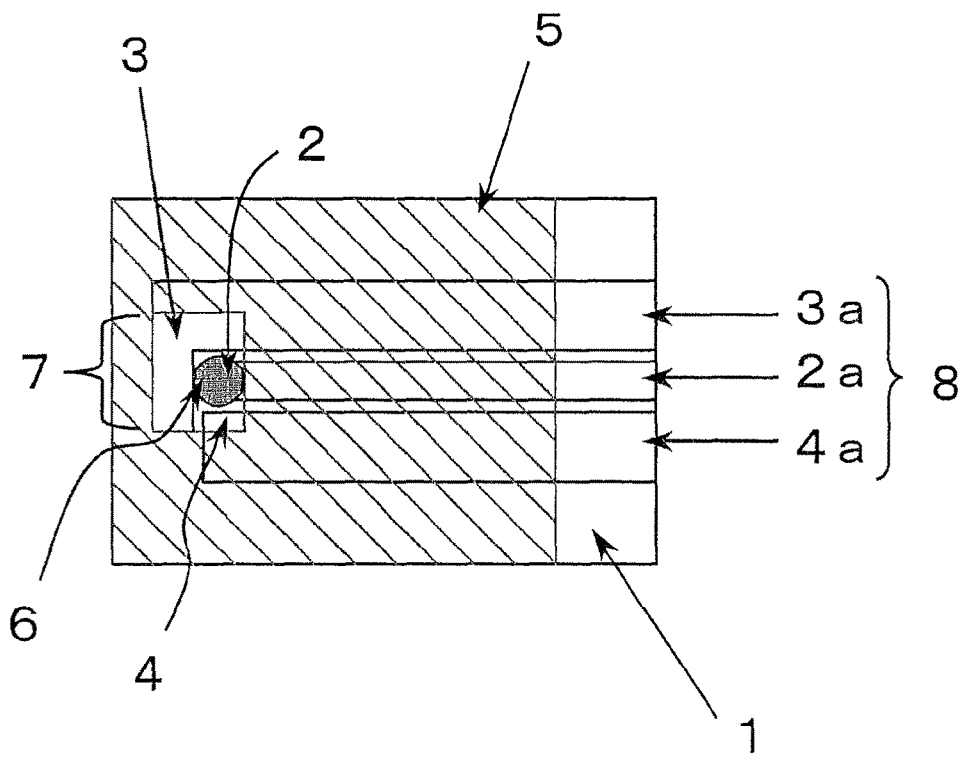
FIG. 1 shows an aspect of the biosensor of the present invention.
Figure 2:
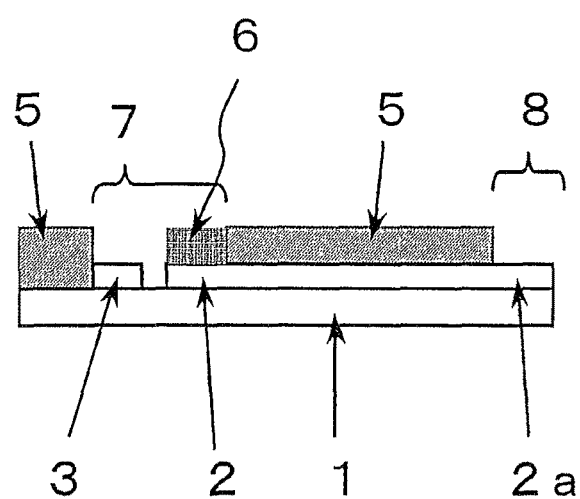
FIG. 2 is a view showing a cross-section surface in almost the center of the working electrode of the biosensor shown in FIG. 1.

First, the structure of the biosensor of the present invention will be described with reference to FIGS. 1 to 4. The biosensor consists of an insulating board 1, an electrode system consisting of a working electrode 2, a counter electrode 3 and a reference electrode 4, an insulating layer 5, a reagent layer 6 formed on the electrode, a specimen-detecting part 7 that does not form the insulating layer 5, a terminal area 2a of the working electrode 2, a terminal area 3a of the counter electrode 3, and a terminal area 4a of the reference electrode 4. The terminal area 2a, the terminal area 3a and the terminal area 4a are comprehensively referred to as a terminal area 8. FIG. 2 shows a cross-section surface in almost the center of the working electrode of the biosensor shown in FIG. 1.

Examples of a material that can be used to form the electrode include gold, platinum, carbon, palladium, silver, and silver-silver chloride.

The insulating board is made of, for example, plastics such as polyethylene terephthalate, polycarbonate or polyvinyl carbonate, or glass. Of these, polyethylene terephthalate is preferable. On such a board, an electrode can be formed by a screen printing method, a vacuum evaporation method, a sputtering method or the like. Of these methods, the screen printing method is preferable. That is to say, it is preferable that an electrode be formed on a polyethylene terephthalate board by the screen printing method using conductive carbon ink.

Figure 3:
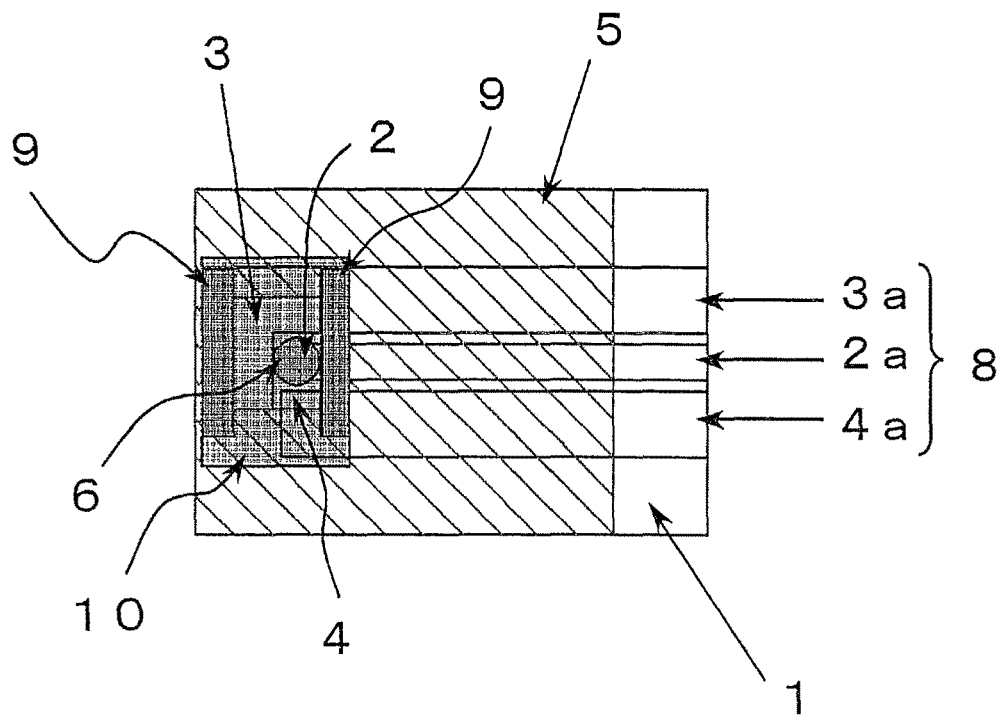
FIG. 3 shows a spacer 9 and a cover 10 that are put in the biosensor of FIG. 1.
Figure 4:
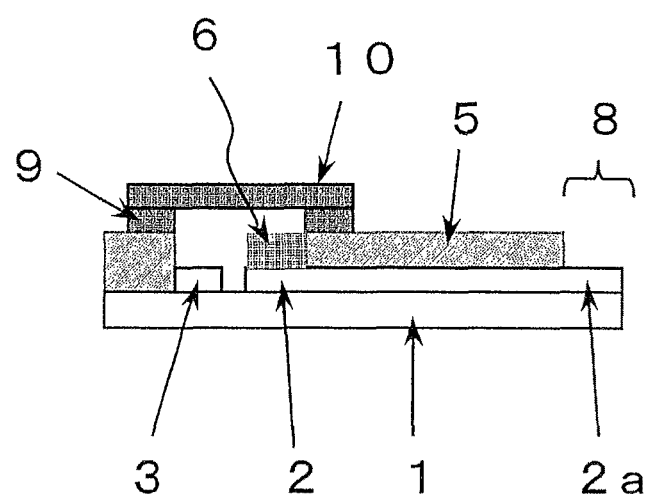
FIG. 4 is a view showing a cross-section surface in almost the center of the working electrode of the biosensor shown in FIG. 3.

Moreover, it may also be a structure, in which a spacer 9 is disposed and a cover 10 is put, as shown in FIG. 3. When such a cover is put, a specimen may be introduced onto the electrode system from either one of two out of the four sides of the cover, on which the spacer is not disposed, utilizing capillarity or the like, for example. FIG. 4 is a view showing a cross-section surface in almost the center of the working electrode of the biosensor shown in FIG. 3.

It is to be noted that these drawings are used to illustrate one example of the electrode structure, and thus that the present invention is not limited to this electrode structure. For example, it is also possible to give the functions of the counter electrode 3 to the reference electrode 4 without putting the counter electrode. The shape of the electrode may also be round and the like.

The reagent layer put in the biosensor of the present invention is formed by a 1,5-AG-measuring enzyme, a phenothiazine compound, and a stabilizer, and as necessary, an acidic polymer compound comprised as an optional ingredient, then dissolving the selected compound(s) in water to prepare an electrode reagent solution, then applying the electrode reagent solution onto the electrode system, and then drying it. The site at which the reagent layer is formed is not particularly limited, as long as it is on the electrode system comprising a working electrode. The concerned site is desirably on the working electrode.

As the aforementioned 1,5-AG-measuring enzyme, 1,5-AG oxidoreductase or the oxidoreductase of a 1,5-AG conversion compound can be used.

As such 1,5-AG oxidoreductase, pyranose oxidase, L-sorbose oxidase, 1,5-AG dehydrogenase, L-sorbose dehydrogenase or the like can be used. As such oxidoreductase of a 1,5-AG conversion compound, 1,5-anhydroglucitol-6-phosphate dehydrogenase (1,5-AG-6-phosphate dehydrogenase) or the like can be used, for example.

Of these, 1,5-AG dehydrogenase is preferable.

As the aforementioned 1,5-AG dehydrogenase, there can be used enzymes derived from: the bacteria belonging to genus *Cytophaga* described in JP 7-67697 A; *Agrobacterium tumefaciens* described in Japanese Patent No. 2872983 and Japanese Patent No. 3819094; *Rahnella aquatilis, Enterobacter cloacae* and *Serratia marcescens* described in JP 11-18762 A; Eumycetes such as *Eupenicillium crustaceum, Hansenura carifonia, Pichia carsonii* and *Pichia pseudopolymorha*, described in JP 2-268679 A; and *Trichoderma longibrachiatum* described in JP 2000-135079 A. Genetically modified enzymes derived from *Pseudomonas* sp. described in PCT/JP2009/061074, which claims priority of Japanese Patent Application No. 2008-159927, are more preferable.

In addition to the aforementioned enzymes, the enzymes described in Patent Literature 1 and Patent Literature 2 can also be used.

As the aforementioned 1,5-AG-6-phosphate dehydrogenase, an enzyme derived from the *Escherichia coli* DH1 strain described in JP 10-84953 A can be used.

The amount of 1,5-AG dehydrogenase used is preferably 0.1 mU to 200 mU, and more preferably 1 mU to 20 mU per chip of the biosensor.

The activity value of 1,5-AG dehydrogenase was determined using, as a substrate, 2-(4-iodophenyl)-3-(4-nitrophenyl)-5-(2,4-disulfophenyl)-2H-tetrazolium monosodium salt (WST-1) (manufactured by Dojindo Laboratories) under the below-mentioned conditions (a reagent composition, procedures and a calculation formula). The amount of an enzyme reacting with 1 μmol WST-1 per minute was defined as 1 unit (U). Specifically, the following method was applied.

Reagent Composition:
(A) 100 mM TAPS (3-(tris(hydroxymethyl)methylamino)propane-1-sulfonic acid) buffer, pH 8.0
(B) 20 mM WST-1/100 mM TAPS buffer
(C) Milli-Q water
(D) 1 M 1,5-AG in Milli-Q water
(E) Enzyme solution in 100 mM TAPS buffer Procedures:
(1) The following reaction mixtures are prepared just before use:
(A) 140 μL, (B) 120 μL, (C) 130 μL, and (D) 200 μL.
(2) The reaction mixture is placed in a glass test tube, and it is preliminarily warmed at 37° C. for 5 minutes.
(3) 10 μL of the enzyme solution (E) is added to the reaction mixture, and the obtained mixture is blended with the use of a vortex. Thereafter, the mixture is rapidly transferred into a quartz cuvette with an optical length of 1 cm that has previously been warmed to 37° C. While maintaining the temperature at 37° C., an increase of the absorbance at 438 nm (Δ438/min) is measured for 1 minute.

Calculation Formula:

$$\text{Enzyme activity (U/mL)} = (\Delta 438/\text{min} \times 0.6 \text{ (mL)} \times \text{dilution magnification of enzyme solution})/(37.0 \times 0.01 \text{ (mL)})$$

Herein, 37.0 indicates the millimolar molecular absorption coefficient of WST-1.

The used amounts of 1,5-AG-measuring enzymes other than the 1,5-AG dehydrogenase can be determined in the same manner as described above.

The phenothiazine compound plays a role as a mediator that donates or receives electrons between the 1,5-AG-measuring enzyme and the electrode.

Examples of the phenothiazine compound include methylene blue, thionine, azure A, azure B, azure C, azure I, toluidine blue, or the like. Of these, thionine is particularly preferable. As such thionine, a salt such as a chloride salt or an acetate is preferably used. Of these, the acetate is particularly preferable. The amount of a phenothiazine compound used is preferably approximately 0.01 nmol to 20 nmol, and more preferably approximately 0.1 nmol to 1 nmol per chip of the biosensor.

As the aforementioned stabilizer, metal salts, organic acids, amino acids (amino acids or salts thereof), and the like can be used. As metal salts, sodium chloride, sodium phosphate, magnesium sulfate and the like are preferable. As organic acids, an organic acid, an organic acid salt, an organic acid anhydride and the like can be used. Preferred examples of such organic acids include sodium citrate, o-sulfobenzoic acid cyclic (2-sulfobenzoic acid anhydride), N-(2-acetamide)-2-aminoethanesulfonic acid (ACES), and piperazin-1,4-bis(2-ethanesulfonic acid) (PIPES). As amino acids or salts thereof, glutamic acid or a salt thereof, lysine or a salt thereof, arginine or a salt thereof, isoleucine or a salt thereof, histidine or a salt thereof, and aspartic acid or a salt thereof are preferable. Of these, sodium chloride, magnesium sulfate and o-sulfobenzoic acid cyclic are more preferable, and o-sulfobenzoic acid cyclic is particularly preferable.

The amount of a stabilizer used is preferably approximately 10 nmol to 2000 nmol, and more preferably approximately 100 nmol to 400 nmol per one biosensor.

The pH of the stabilizer is preferably from pH 5 to pH 11.

These stabilizers may be used singly or in combination of two or more.

When an acidic polymer compound is used as an optional ingredient, it makes possible to precisely measure the concentration of 1,5-AG contained in a wide range of specimens without being affected by hematocrit and the like in the measurement of 1,5-AG in a specimen, in which whole blood is used as such a specimen. Thus, it is preferable to use such an acidic polymer compound in the biosensor of the present invention. An example of the acidic polymer compound used as an optional ingredient is a hydrocarbon compound that has an acidic functional group such as a sulfonic acid group, a phosphoric acid group or a carboxy group and may be substituted with a fluorine atom. Examples of such an acidic polymer compound include: a sulfonated poly(4-phenoxybenzoyl-1,4-phenylene) resin; an aromatic condensation polymer such as an alkylsulfonated polybenzoimidazole resin; a perfluorosulfonic acid resin such as Nafion (registered trademark; manufactured by Du Pont, CAS Reg. No. 31175-20-9); Aciplex (manufactured by Asahi Kasei Corporation); a carboxy group-containing perfluorocarbon (Flemion S membrane) (manufactured by Asahi Glass Co., Ltd.); polyether sulfone resins described in Japanese Patent No. 4324518 and JP 2008-291224 A; alginic acid or a salt thereof; and carboxymethylcellulose. Of these, Nafion (registered trademark) as a perfluorosulfonic acid resin is particularly preferable.

If Nafion (registered trademark) is used as the above described acidic polymer compound, the amount used is preferably approximately 0.01 mg to 10.0 mg, and more preferably approximately 0.2 mg to 0.6 mg per one biosensor. When other types of acidic polymer compounds are used as well, the amounts used may be arbitrarily determined depending on the properties of a compound used.

The acidic polymer compound, as well as a 1,5-AG-measuring enzyme, a phenothiazine compound, a stabilizer and the like, are used to prepare an electrode reagent solution. Thereafter, the electrode reagent solution is applied onto the electrode system and is then dried, so as to prepare a reagent layer. Alternatively, the electrode reagent solution comprising a 1,5-AG-measuring enzyme, a phenothiazine compound, a stabilizer and the like may be prepared. Thereafter, the prepared solution may be applied onto the electrode system and may be then dried to prepare a reagent layer. Subsequently, an acidic polymer compound that has been adjusted in an appropriate concentration may be applied on the aforementioned reagent layer and may be then dried for lamination, thereby forming a reagent layer consisting of two layers.

A drying method may be selected, as appropriate, from among vacuum drying, thermal drying, natural drying, freeze-drying and the like.

Moreover, the aforementioned reagent layer may comprise a reagent for converting 1,5-AG to a 1,5-AG conversion compound, as necessary.

As a method of disposing an electrode reagent solution on an electrode system, there may be applied a method of forming a thin film using a spin-coater, a method of dipping a biosensor in an electrode reagent solution, etc., as well as coating and drying.

It may also be possible that an electrode reagent solution be immobilized on an electrode system or a flow channel, using a polymer membrane, a resin and the like. The term "flow channel" is used herein to mean a route through which a specimen passes, when the position on which a specimen is spotted is apart from the electrode system.

Next, a method for electrochemically measuring 1,5-AG using the above described biosensor will be described.

As an electrochemical detector, GPIB RS232C-equipped 8CH Multi-Potentiostat MODEL PS-08, manufactured by Toho Technical Research Co., Ltd., is used, for example. With this detector, the terminal areas of the working electrode, reference electrode and counter electrode of the above described biosensor are connected. A specimen to be measured is preferably mixed with a glucose-converting reagent as described later, and the obtained mixture is then spotted on the electrode of a biosensor in which a reagent layer is disposed. Thereafter, a certain amount of voltage is applied thereto, so as to obtain a 1,5-AG measurement value.

Hereinafter, the term "voltage" indicates the voltage of a working electrode to a silver/silver chloride reference electrode.

A glucose-converting reagent means a reagent, a carrier or the like, which is used to convert glucose contained in a specimen to a conversion compound that does not react with a 1,5-AG-measuring enzyme, or to remove such glucose by an ion exchange method or the like. Even in the case of healthy persons, the concentration of 1,5-AG in whole blood is approximately a hundredth of the concentration of glucose contained therein. Thus, if glucose is present during the measurement of 1,5-AG using the enzyme, it causes errors. The glucose-converting reagent is preferably used, when 1,5-AG in a specimen containing glucose is measured.

For example, 17.6 mM $MgCl_2$, 17.6 mM KCl, 175.7 mM phosphoenol pyruvate (PEP), 17.6 mM ATP, 123 U/mL pyruvate kinase (PK), 75 U/mL glucokinase, 200 U/mL ascorbate oxidase, 100 mM NaCl, 0.1% $NaN_3$, 0.1 mM EDTA (ethylenediaminetetraacetic acid), and 0.06% BSA (bovine serum albumin) are dissolved and mixed in 10.0 mM 2-(N-morpholino)ethanesulfonic acid (MES) buffer (pH 7.0) described in Patent Literature 2. The obtained mixture may be adjusted to pH 7.0 with the use of 1 N sodium hydroxide aqueous solution, and it may be then used as a glucose-converting reagent.

With regard to the mixing ratio between a glucose-converting reagent and a specimen, the glucose-converting reagent may be mixed with the specimen, so that the specimen may be used at a volume ratio of 0.01 to 2 with respect to 1 volume of the glucose-converting reagent.

The applied voltage may be selected, as appropriate, depending on a phenothiazine compound used. For example, thionine acetate is used, a voltage of approximately 0 V is adequate. The time at which the voltage is applied may be determined to such an extent that a measurement value can be obtained in proportion to the concentration of 1,5-AG and reproducibility can be obtained in measurements. The time at which the voltage is applied is preferably approximately 2 seconds to 5 minutes, and more preferably approximately 30 seconds to 3 minutes.

Before application of the voltage, a voltage that is approximately 0.1 V lower than the aforementioned voltage may be applied for approximately 3 to 20 seconds. Thereby, there may be a case in which measurement errors found among biosensors could be overcome. When the measurement is carried out using thionine acetate, for example, it is appropriate to apply a voltage of −0.1 V for approximately 10 seconds.

In order to measure 1,5-AG, a suitable parameter obtained from a decay curve of time and current, obtained by application of the voltage, can be used as a measurement value. Specifically, a current value obtained after a certain period of time has passed after application of the voltage, or a charge amount within a certain period of time, may be used. For example, a current value at 5 seconds after application of the voltage or a charge amount for 100 seconds after application of the voltage may be used.

Herein, amperometry and coulometry have been described. However, it may also be possible to apply cyclic voltammetry and to use the obtained peak strength as a measurement value.

The present invention includes a method for electrochemically measuring 1,5-AG contained in a specimen, using the above described biosensor. However, such an electrochemically measuring method is not limited to the measurement methods as specifically described above.

The present invention includes a kit for measuring 1,5-anhydroglucitol contained in whole blood, which comprises at least the above described biosensor, and for example, a puncture device and a whole blood-collecting device, which are used in collection of the whole blood. The puncture device may be the same device as a puncture device included with a common blood glucose self-monitoring meter. This kit may further comprise a glucose-converting reagent.

As a method of retaining a glucose-converting reagent, a method of fractionating a specimen, a method of mixing a specimen with a glucose-converting reagent, and a method of spotting it on an electrode, a person skilled in the art or a patient may select a suitable method for the measurement, as appropriate. For example, there can be applied a method, which comprises: retaining a glucose-converting reagent in a hermetically sealable, small vessel, such as a microtube; fractionating a specimen using the capillary described in Patent Literature 2 or the like; mixing the specimen as is with the glucose-converting reagent contained in the small vessel by pipetting; and spotting the obtained mixture onto the electrode using the capillary. Moreover, it is also possible to retain a glucose-converting reagent in a dry state on the biosensor, fractionate whole blood used as a specimen according to a capillarity, mix the whole blood with the glucose-converting reagent on the biosensor, and then directly introduce the mixture onto an electrode via a flow channel. As a method of retaining a glucose-converting reagent on a biosensor, other than the coating and drying method, such a glucose-converting reagent may be immobilized on an electrode system or on a flow channel, using a polymer membrane, a resin, etc. There are no problems even though it is a position on which a specimen is to be spotted. The term "flow channel" is used herein to mean a route through which a specimen passes, when the position on which a specimen is spotted is apart from the electrode system.

The method of retaining a glucose-converting reagent, the method of fractionating a specimen, the method of mixing the specimen with the glucose-converting reagent, and the method of spotting the mixture on an electrode, as described above, are not intended to limit the scope of the present invention.

Hereinafter, the present invention will be described in detail in the following examples. However, these examples are used for illustrative purposes only, and thus they are not intended to limit the scope of the present invention.

EXAMPLES

Example 1

Biosensor for Measuring 1,5-AG, Which Has Reagent Layer Comprising Genetically Modified 1,5-AG Dehydrogenase, Thionine Acetate, O-sulfobenzoic Acid Cyclic and Nafion
1. Preparation of Biosensor Genetically modified 1,5-AG dehydrogenase derived from *Pseudomonas* sp. described in PCT/JP2009/061074, which claims priority of Japanese Patent Application No. 2008-159927, was used as a 1,5-AG-measuring enzyme. (Specifically, there was used 1,5-AG dehydrogenase Ver. 3.2, one of genetically modified enzymes derived from *Pseudomonas* sp. described in PCT/JP2009/061074, which consisted of an amino acid sequence in which the alanine residue at position 4 was substituted with a glycine residue, the threonine residue at position 14 was substituted with a serine residue, the arginine residue at position 37 was substituted with a threonine residue, the glycine residue at position 67 was substituted with a glutamic acid residue, the tyrosine residue at position 80 was substituted with an asparagine residue, the methionine residue at position 93 was substituted with a valine residue, the proline residue at position 156 was substituted with an arginine residue, the aspartic acid residue at position 202 was substituted with an asparagine residue, the alanine residue at position 235 was substituted with a threonine residue, the tyrosine residue at position 348 was substituted with an asparagine residue, and the alanine residue at position 473 was substituted with a valine residue, with respect to the amino acid sequence shown in SEQ ID NO: 1). Thionine acetate was used as a phenothiazine compound, o-sulfobenzoic acid cyclic was used as a stabilizer, and Nafion (registered trademark) was used as an acidic polymer compound. Using these components, an electrode reagent solution was prepared. With regard to the amounts of individual components per a sensor chip, it was 6.52 mU in the case of 1,5-AG dehydrogenase, it was 0.24 nmol in the case of thionine acetate, it was 100 nmol in the case of o-sulfobenzoic acid cyclic, and it was 0.2 mg in the case of Nafion (registered trademark).

Carbon was used as a working electrode, carbon was also used as a counter electrode, and silver/silver chloride was used as a reference electrode. These components were applied onto an electrode according to screen printing. Thereafter, the prepared electrode reagent solution was applied onto the electrode, and it was then dried in a 50° C. incubator for 5 minutes, so as to obtain a biosensor comprising a reagent layer, which was to be used in the measurement of 1,5-AG.
2. Evaluation of Stability of Biosensor This biosensor was connected via a terminal area with GPIB RS232C-equipped 8CH Multi-Potentiostat MODEL PS-08, manufactured by Toho Technical Research Co., Ltd.

As specimens, 0 μg/mL and 50 μg/mL 1,5-AG standard solutions were used. Each standard solution was mixed with the above described glucose-converting reagent (specifically, the reagent of Patent Literature 2) at a mixing ratio of 1:2, and the obtained mixture was then spotted on the electrode comprising the reagent layer, followed by conducting the measurement. The measurement was carried out by applying a voltage of –0.1 V for 10 seconds and then applying a voltage of 0 V for 100 seconds. A charge amount for 100 seconds during which a voltage of 0 V was applied was measured.

The stability of the biosensor was evaluated by an accelerated test at 55° C. The biosensor produced by the above described method, together with silica gel, was hermetically sealed, and they were then stored at 55° C. for a certain period of time. By this accelerated test, the stability of the biosensor at room temperature can be anticipated.

Figure 5:
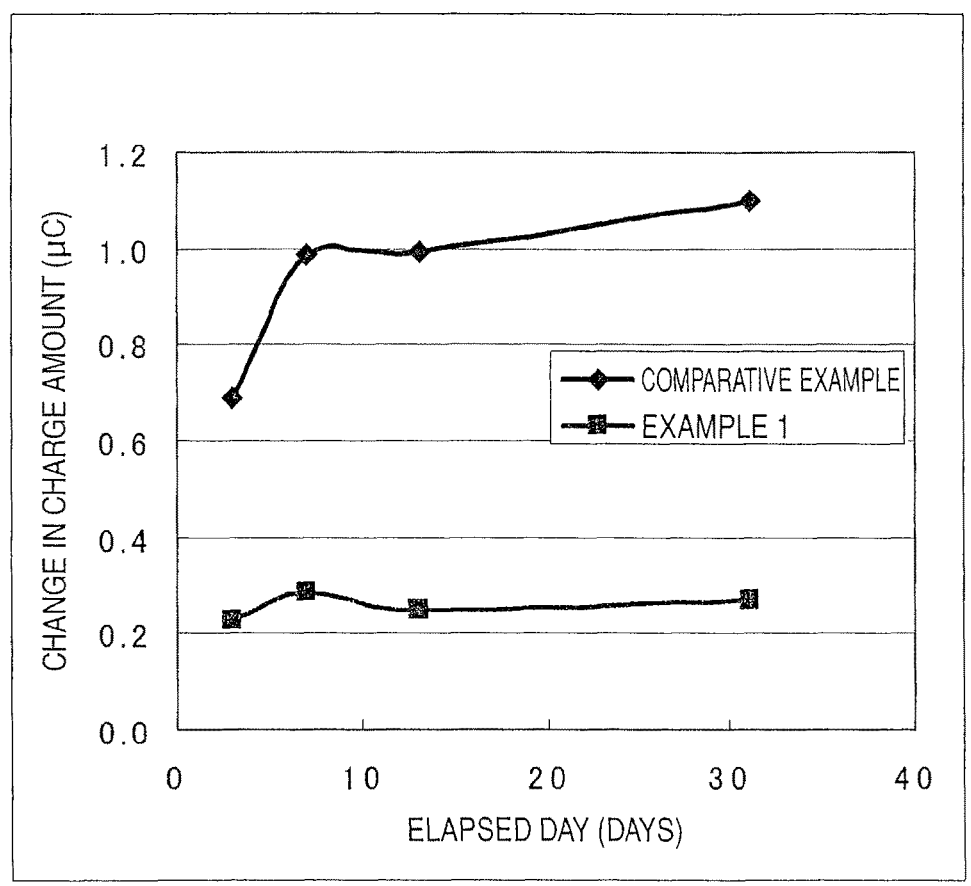
FIG. 5 is a graph obtained by measuring 0 μg/mL 1,5-AG using the biosensor of Example 1 and the biosensor of the Comparative Example, which have been stored at 55° C. for a certain period of time.

With regard to 50 μg/mL 1,5-AG used as a blank, a change in the charge amount over time is shown in FIG. 5.

Figure 6:
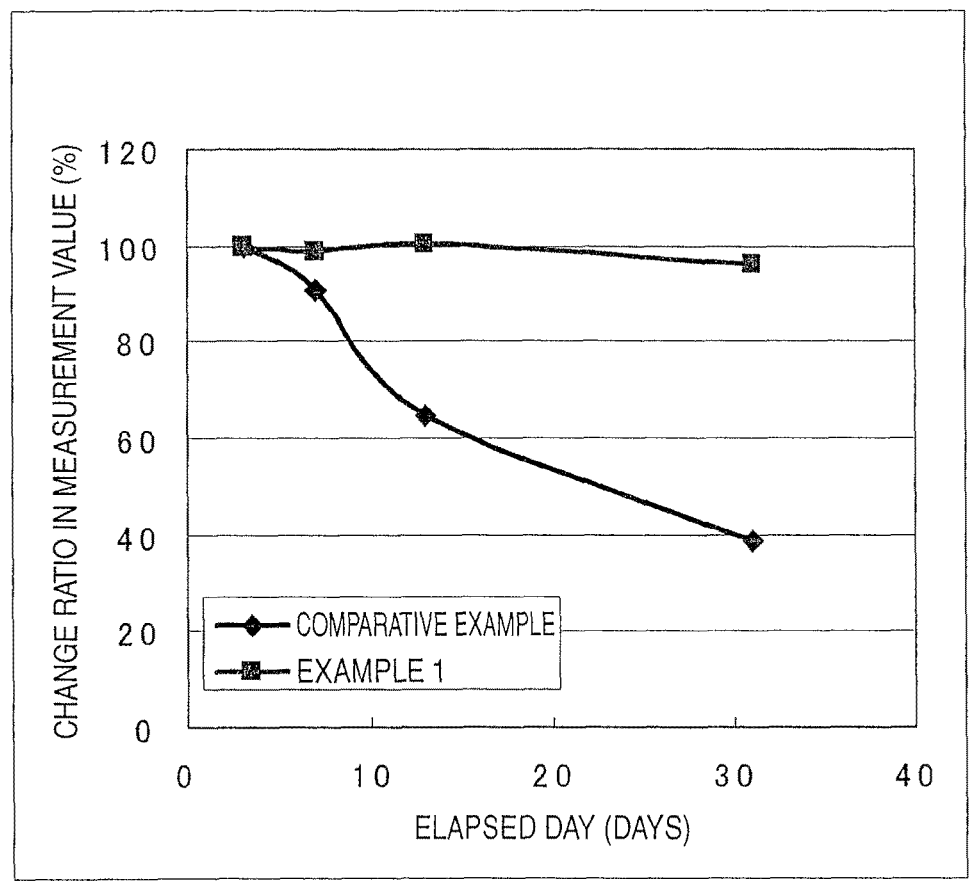
FIG. 6 is a graph obtained by measuring 50 μg/mL 1,5-AG using the biosensor of Example 1 and the biosensor of the Comparative Example, which have been stored at 55° C. for a certain period of time.

With regard to 50 μg/mL 1,5-AG used as a signal, the measurement value on the $3^{rd}$ day after production of the biosensor was defined as an origin, and the subsequent measurement values were expressed as change ratios. A change over time is shown in FIG. 6. The measurement value of 50 μg/mL 1,5-AG on the $x^{th}$ day after production of the biosensor was divided by the measurement value of 50 μg/mL 1,5-AG on the $3^{rd}$ day after production of the biosensor. The obtained value was defined as a change ratio after the storage of the biosensor for x days. X was defined as the value of an x-axis.

Comparative Example

Biosensor for Measuring 1,5-AG, Which Has Reagent Layer Comprising Neither Stabilizer nor Acidic Polymer Compound As a comparative example, an electrode reagent solution was prepared without using a stabilizer and an acidic polymer compound. Thereafter, a biosensor comprising a reagent layer was produced in the same manner as that of Example 1. The biosensor was subjected to the same test as that conducted in Example 1.

A change over time in the charge amount of 0 μg/mL 1,5-AG used as a blank is shown in FIG. 5. A change over time in the charge amount of 50 μg/mL 1,5-AG is shown in FIG. 6.

As is clear from FIG. 5 and FIG. 6, the storage stability of the biosensor of Example 1 was significantly improved when compared with that of the comparative example. Even after the storage, the biosensor was able to conduct the measurement equivalent to that at the initiation of the production of the biosensor. On the other hand, the measurement value of 0 μg/mL 1,5-AG used as a blank became lower than that of the comparative example, and the S/N ratio was improved, so that the sensitivity of the measurement could also be improved.

Example 2

Biosensor for Measuring 1,5-AG, Which Has Reagent Layer Comprising Genetically Modified 1,5-AG Dehydrogenase, Thionine Acetate and O-sulfobenzoic Acid Cyclic 1. Preparation of Biosensor The same 1,5-AG dehydrogenase derived from *Pseudomonas* sp. as that used in Example 1 was used as a 1,5-AG-measuring enzyme, thionine acetate was used as a phenothiazine compound, and o-sulfobenzoic acid cyclic was used as a stabilizer, so as to prepare an electrode reagent solution. With regard to the amounts of individual components per a sensor chip, it was 6.52 mU in the case of 1,5-AG dehydrogenase, it was 024 nmol in the case of thionine acetate, and it was 100 nmol in the case of o-sulfobenzoic acid cyclic.

Carbon was used as a working electrode, carbon was also used as a counter electrode, and silver/silver chloride was used as a reference electrode. These components were applied onto an electrode according to screen printing. Thereafter, the prepared electrode reagent solution was applied onto the electrode, and it was then dried in a 50° C. incubator for 5 minutes. Subsequently, Nafion (registered trademark) was applied as an acidic polymer onto a reagent layer, resulting in an amount of 0.2 mg per a sensor chip, and it was then dried for lamination, so as to obtain a biosensor, which was to be used in the measurement of 1,5-AG 2. Measurement of 1,5-AG Contained in Whole Blood Specimen by Biosensor This biosensor was connected via a terminal area with GPIB RS232C-equipped 8CH Multi-Potentiostat MODEL PS-08, manufactured by Toho Technical Research Co., Ltd.

As a specimen, human whole blood was used, and the human whole blood was mixed with the above described glucose-converting reagent at a mixing ratio of 1:2. Thereafter, the obtained mixture was spotted on the electrode comprising the reagent layer, followed by conducting the measurement. The measurement was carried out by applying a voltage of −0.1 V for 10 seconds and then applying a voltage of 0 V for 100 seconds. A current amount was measured 5 seconds after initiation of the application of the voltage.

A standard solution prepared by adding a 1,5-AG standard product to SeraSub (registered trademark; manufactured by CST Technology) was measured, and using the obtained current value, a standard calibration curve was prepared. Using the standard calibration curve, the current value of the specimen was calculated relative to the 1,5-AG concentration.

The same human whole blood specimen as described above was subjected to plasma skimming, and the 1,5-AG concentration of the obtained plasma was then obtained using Lana$^R$ 1,5-AG Auto Liquid (manufactured by Nippon Kayaku Co., Ltd.). The correlation between the thus obtained 1,5-AG concentration and the concentration obtained by the present electrochemical measurement is shown in FIG. 7.

Figure 7:
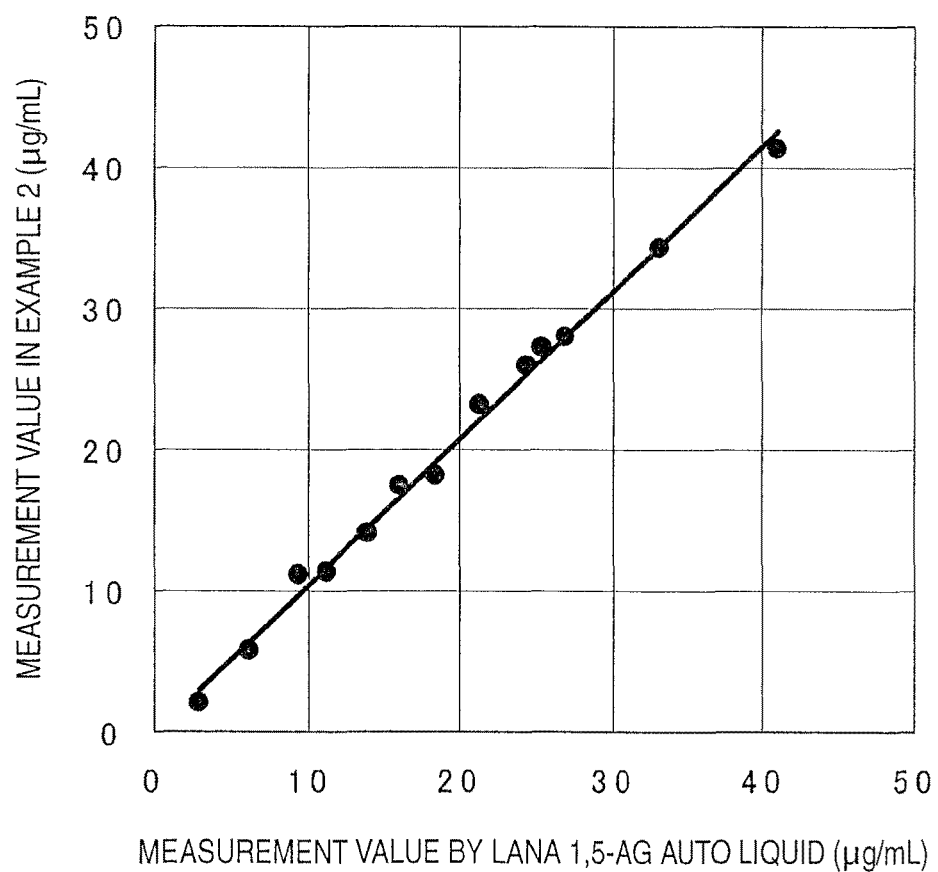
FIG. 7 is a graph showing the correlation between a 1,5-AG concentration in a whole blood specimen obtained using the biosensor of Example 2 and a 1,5-AG concentration obtained by measuring a plasma obtained from the same specimen as described above using Lana$^R$ 1,5-AG Auto Liquid.

As is clear from FIG. 7, the slope of the correlation is 1.04. The intercept of the correlation is −0.05. With regard to the correlation coefficient, $R^2$=0.9946. Thus, the two measurement values had an extremely good correlation.

Example 3

Biosensor for Measuring 1,5-AG, Which Has Reagent Layer Comprising Genetically Modified 1,5-AG Dehydrogenase, Thionine Acetate and Various Types of Stabilizers The same 1,5-AG-measuring enzyme and thionine acetate as those used in Example 1 were used. As a stabilizer, each substance shown in the following Table 1 was used, and Nafion (registered trademark) was used as an acidic polymer compound in several cases. Using these components, biosensors were produced in the same manner as that in Example 1. Thereafter, a test was carried out by the same method as that in Example 1 using a 50 μg/mL 1,5-AG solution. The change ratio after the storage for 30 days is shown in Table 1.

TABLE 1

Storage stability of biosensor achieved by use of various types of stabilizers

| Stabilizer | Change ratio after storage for 30 days (%) |
|---|---|
| Control | 38.7 |
| Sodium chloride | 95.4 |
| Sodium citrate | 86.7 |
| Magnesium sulfate | 97.4 |
| o-Sulfobenzoic acid cyclic | 93.6 |
| Glutamic acid | 84.1 |
| Lysine | 78.7 |
| Arginine | 86.6 |
| Isoleucine | 56.1 |
| Histidine | 74.7 |
| Aspartic acid | 62.9 |
| Myoinositol | 65.8 |
| Saccharose | 69.1 |
| Maltose | 91.9 |
| Raffinose | 86.6 |
| Nafion + PIPES | 96.5 |
| Nafion + disodium 3-sulfobenzoate | 88.0 |
| Nafion + o-sulfobenzoic acid cyclic | 95.9 |
| Alginic acid + PIPES | 87.1 |
| Disodium 3-sulfobenzoate + PIPES | 95.3 |
| o-Sulfobenzoic acid cyclic + PIPES | 97.0 |
| Alginic acid + disodium 3-sulfobenzoate | 63.3 |
| Alginic acid + o-sulfobenzoic acid cyclic | 89.5 |
| o-Sulfobenzoic acid cyclic + sodium chloride | 65.3 |
| PIPES + sodium chloride | 67.4 |

In the table, a test, in which two types of stabilizers and/or acidic polymers were used, is indicated by the symbol +.

As is clear from the results shown in Table 1, it is found that the storage stability of the biosensor becomes excellent by using various types of stabilizers.

Industrial Applicability

According to the present invention, it becomes possible to prevent the deterioration of a biosensor due to a change in environmental factors such as a temperature applied during storage, and to produce a biosensor with improved storage stability, which suppresses a change in 1,5-AG measurement values and is able to precisely measure a low 1,5-AG value. Thus, even after long-term storage, there can be obtained the same precise 1,5-AG measurement value as that at initiation of the production. Moreover, it is also possible to provide a biosensor capable of precisely measuring a 1,5-AG value in a wide range of specimens without being affected by hematocrit and the like during whole blood measurement.

| Reference Signs List | |
|---|---|
| 1 | Insulating board |
| 2 | Working electrode |
| 2a | Terminal area of working electrode |
| 3 | Counter electrode |
| 3a | Terminal area of counter electrode |
| 4 | Reference electrode |
| 4a | Terminal area of reference electrode |
| 5 | Insulating layer |
| 6 | Reagent layer |
| 7 | Specimen-detecting part |
| 8 | Terminal area |
| 9 | Spacer |
| 10 | Cover |

The invention claimed is:

1. A biosensor having an electrode system for electrochemically measuring 1,5-anhydroglucitol and a reagent layer formed on the electrode system, wherein the reagent layer comprises:
   (1) a 1,5-anhydroglucitol-measuring enzyme;
   (2) a phenothiazine compound;
   (3) a stabilizer consisting of one or two or more compounds selected from the group consisting of sodium chloride, sodium citrate, magnesium sulfate, piperazin-1,4-bis(2-ethanesulfonic acid), o-sulfobenzoic acid cyclic, arginine or a salt thereof, glutamic acid or a salt thereof, and lysine or a salt thereof; and
   (4) an acidic polymer compound as an optional ingredient.

2. The biosensor according to claim 1, wherein the 1,5-anhydroglucitol-measuring enzyme is 1,5-anhydroglucitol dehydrogenase or 1,5-anhydroglucitol-6-phosphate dehydrogenase.

3. The biosensor according to claim 1, wherein the phenothiazine compound is thionine.

4. The biosensor according to claim 1, wherein the stabilizer is o-sulfobenzoic acid cyclic.

5. The biosensor according to claim 1, wherein the acidic polymer compound is a hydrocarbon compound, which has an acidic functional group and may be substituted with a fluorine atom.

6. The biosensor according to claim 1, wherein the acidic polymer compound is a perfluorosulfonic acid resin.

7. The biosensor according to claim 1, wherein the 1,5-anhydroglucitol-measuring enzyme used is 1,5-anhydroglucitol dehydrogenase derived from *Pseudomonas* sp.

8. A method for electrochemically measuring 1,5-anhydroglucitol contained in a specimen using the biosensor according to claim 1.

9. A kit for electrochemically measuring 1,5-anhydroglucitol contained in a specimen, the kit comprising the biosensor according to claim 1.

* * * * *

SEQUENCE LISTING

<160> NUMBER OF SEQ ID NOS: 1

<210> SEQ ID NO 1
<211> LENGTH: 496
<212> TYPE: PRT
<213> ORGANISM: Artificial Sequence
<220> FEATURE:
<223> OTHER INFORMATION: Protein expressed by mutated 1,5-anhydroglucitol dehydrogenase gene

<400> SEQUENCE: 1

```
Met Glu Phe Ala Gly Gln Pro Asp Ile Val Ile Ile Gly Thr Gly Ile
 1               5                  10                  15

Gly Gly Ala Ser Ile Ala Ala Gly Leu Ser Ala Ser Gly Ala Asp Ile
                20                  25                  30

Leu Ile Leu Glu Arg Gly Glu Ser Leu Pro Asp Arg Pro Glu Asn Arg
            35                  40                  45

Asp Gln His Ala Ile Phe Gln Arg Gly Phe Phe Arg Pro Lys Glu Phe
        50                  55                  60

Trp Tyr Gly Thr Asp Gly Thr Pro Phe Asn Pro Gly Asn Tyr Tyr Tyr
 65                  70                  75                  80

Val Gly Gly Asn Ser Lys Phe Tyr Gly Ala Val Leu Met Arg Tyr Arg
                85                  90                  95

Arg Glu Asp Phe Glu Glu Leu Ala His Leu Glu Gly Val Ser Pro Ala
            100                 105                 110

Trp Pro Phe Ala Tyr Asp Glu Leu Glu Pro Trp Tyr Cys Lys Ala Glu
        115                 120                 125

Glu Leu Phe Gln Val Arg Gly Glu Leu Gly Asp Asp Pro Thr Glu Pro
    130                 135                 140

Tyr His Ser Lys Pro Tyr Ser Tyr Pro Ala Ile Pro Asp Glu Ser Pro
145                 150                 155                 160

Ile Ala Asp Met Arg Ala Arg Leu Lys Lys Ala Gly Leu His Pro Ala
                165                 170                 175

Ser Leu Pro Leu Gly Val Asp Ile Glu Arg Trp Leu Ala Lys Ala Lys
            180                 185                 190

Thr Pro Trp Asp Ala His Pro Asn Ser Asp Asp Gly Lys Met Asp Ala
        195                 200                 205

Glu Thr Cys Pro Leu Ala Leu Ala Leu Lys His Pro Asn Val Gly Leu
    210                 215                 220

Glu Thr Ser Ala Arg Val Thr Lys Leu Glu Ala Gly Pro Asp Gly Lys
225                 230                 235                 240

Thr Ile Val Ala Val His Tyr Val Lys Asn Gly Glu Ala Leu Val Leu
                245                 250                 255

Arg Pro Lys Leu Val Ile Leu Ser Ala Gly Ala Val Gln Ser Ala Ala
            260                 265                 270
```

-continued

```
Leu Leu Leu Arg Ser Gly Leu Ala Asn Arg Ser Asp Gln Val Gly Arg
        275                 280                 285

Asn Phe Met Asn His Asn Ala Ser Ala Val Ile Gly Phe Asp Pro Arg
    290                 295                 300

Tyr Arg Asn Asp Ser Val Tyr Gln Lys Thr Phe Gly Phe Asn Asp Tyr
305                 310                 315                 320

Tyr Leu Ser Asp Gly Ala Gly Gly Pro Pro Leu Gly Asn Val Gln Leu
                325                 330                 335

Leu Gly Arg Val Ser Gly Ala Ile Leu Lys Ser Tyr Met Arg Gln Val
            340                 345                 350

Pro Glu Trp Phe Leu Asn Arg Ile Ala Arg His Thr Ile Asp Phe Tyr
        355                 360                 365

Ala Met Ser Glu Asp Leu Pro Ser Pro Glu Ser Arg Val Ser Val Asp
    370                 375                 380

Gly Asp Arg Ile Ile Leu His Trp Val Arg Ser Asn Trp Lys Ala His
385                 390                 395                 400

Leu Met Leu Val Asp Lys Leu Lys Ser Ala Leu Arg Ala Ala Gly Phe
                405                 410                 415

Pro Val Val Leu Ser Arg Ala Phe Asp Arg Arg Thr Pro Ser His Gln
            420                 425                 430

Cys Gly Thr Val Arg Ile Gly Asp Asn Pro Ala Thr Ala Pro Leu Asp
            435                 440                 445

Pro Tyr Cys Arg Ala Tyr Asp His Pro Asn Leu Tyr Val Val Asp Ala
        450                 455                 460

Ser Phe Leu Pro Thr Ser Ala Ala Ala Asn Pro Ala Leu Thr Ile Ala
465                 470                 475                 480

Ala Gln Ala Leu Arg Val Ala Asp His Leu Asn Arg Glu Val Leu Ala
                485                 490                 495
```